(12) United States Patent
Li et al.

(10) Patent No.: US 7,528,261 B2
(45) Date of Patent: May 5, 2009

(54) SMALL MOLECULE COMPOUND HAVING INDOLOCARBAZOLE MOIETY AND DIVALENT LINKAGE

(75) Inventors: Yuning Li, Mississauga (CA); Beng S Ong, Singapore (SG); Yiliang Wu, Mississauga (CA); Ping Liu, Mississauga (CA)

(73) Assignee: Xerox Corporation, Norwalk, CT (US)

( * ) Notice: Subject to any disclaimer, the term of this patent is extended or adjusted under 35 U.S.C. 154(b) by 0 days.

(21) Appl. No.: 11/957,927

(22) Filed: Dec. 17, 2007

(65) Prior Publication Data

US 2008/0103314 A1    May 1, 2008

Related U.S. Application Data

(62) Division of application No. 11/280,552, filed on Nov. 16, 2005, now Pat. No. 7,396,852.

(51) Int. Cl.
*C07D 207/00* (2006.01)
*C07D 333/08* (2006.01)

(52) U.S. Cl. ........................................ 548/400; 549/83
(58) Field of Classification Search ................. 514/430; 549/200, 429; 548/400
See application file for complete search history.

(56) References Cited

U.S. PATENT DOCUMENTS

| | | | |
|---|---|---|---|
| 5,843,607 A | 12/1998 | Hu et al. | |
| 5,942,340 A | 8/1999 | Hu et al. | |
| 5,952,115 A | 9/1999 | Hu et al. | |
| 6,045,822 A | 4/2000 | Kato et al. | |
| 6,949,762 B2 | 9/2005 | Ong et al. | |
| 7,173,140 B2 | 2/2007 | Li et al. | |
| 7,294,850 B2 | 11/2007 | Ong et al. | |
| 7,396,852 B2 * | 7/2008 | Li et al. | 514/417 |
| 2006/0124923 A1 | 6/2006 | Wu et al. | |
| 2006/0214155 A1 | 9/2006 | Ong et al. | |
| 2007/0112167 A1 | 5/2007 | Li et al. | |

OTHER PUBLICATIONS

Christos D. Dimitrakopoulos et al., "Organic Thin Film Transistors for Large Area Electronics," *Adv. Mater.*, vol. 14, No. 2, pp. 99-117 (2002).

Salem Wakim et al., "Organic Microelectronics: Design, Synthesis, and Characterization of 6,12-Dimenthylindolo[3,2-b]Carbazoles," *Chem. Mater.* vol. 16, No. 23, pp. 4386-4388 (published on web Jul. 7, 2004).

Nan-Xing Hu et al., "5-11-Dihydro-5,11-di-1-naphthylindolo[3,2-b]carbazole: Atropisomerism in a Novel Hole-Transport Molecule for Organic Light-Emitting Diodes," *J. Am. Chem. Soc.*, vol. 121, pp. 5097-5098 (1999).

* cited by examiner

*Primary Examiner*—Golam M. M. Shameem
*Assistant Examiner*—Susannah Chung
(74) *Attorney, Agent, or Firm*—Zosan Soong

(57) ABSTRACT

A small molecule compound including at least one type of an optionally substituted indolocarbazole moiety and at least one divalent linkage.

6 Claims, 2 Drawing Sheets

US 7,528,261 B2

SMALL MOLECULE COMPOUND HAVING INDOLOCARBAZOLE MOIETY AND DIVALENT LINKAGE

CROSS-REFERENCE TO RELATED APPLICATIONS

This application is a divisional application of co-pending U.S. application Ser. No. 11/280,552, filing date Nov. 16, 2005, from which priority is claimed, the disclosure of which is totally incorporated herein by reference.

Yuning Li et al., U.S. application Ser. No. 11/280,795, filed Nov. 16, 2005, titled "DEVICE CONTAINING COMPOUND HAVING INDOLOCARBAZOLE MOIETY AND DIVALENT LINKAGE," published as US 2007/0112167.

Beng S. Ong et al., U.S. application Ser. No. 10/865,620, filed Jun. 10, 2004, titled "DEVICE WITH SMALL MOLECULAR THIOPHENE COMPOUND HAVING DIVALENT LINKAGE," now U.S. Pat. No. 7,294,850.

Yiliang Wu et al., U.S. application Ser. No. 11/167,485, filed Jun. 27, 2005, titled "THIN FILM TRANSISTORS INCLUDING INDOLOCARBAZOLES," published as US 2006/0124923.

Beng S. Ong et al., U.S. application Ser. No. 11/167,512, filed Jun. 27, 2005, titled "COMPOUND WITH INDOLOCARBAZOLE MOIETIES AND DEVICES CONTAINING SUCH COMPOUND," published as US 2006/0214155.

STATEMENT REGARDING FEDERALLY SPONSORED RESEARCH OR DEVELOPMENT

This invention was made with United States Government support under Cooperative Agreement No. 70NANBOH3033 awarded by the National Institute of Standards and Technology (NIST). The United States Government has certain rights in the invention.

BACKGROUND OF THE INVENTION

Organic electronics has been an intense research topic over the last two decades or so because of their enormous commercial potential. Some illustrative organic electronic devices are diodes, organic thin film transistors, and organic photovoltaics. One of the key components in these devices is organic semiconductors which have received extensive research and development efforts. In the field of organic electronics, organic thin film transistors (OTFTs) have in recent years attracted great attention as a low-cost alternative to mainstream amorphous silicon-based transistors for electronic applications. OTFTs are particularly suited for applications where large-area circuits (e.g., backplane electronics for large displays), desirable form factors and structural features (e.g., flexibility for "electronic paper"), and affordability (e.g., ultra low cost for ubiquitous radio frequency identification tags) are essential.

Organic semiconductors are typically based on: (1) acenes such as tetracene, pentacene and their derivatives, (2) thiophenes such as oligothiophenes and polythiophenes, (3) fused-ring thiophene-aromatics and thiophene-vinylene/arylene derivatives. Most of these semiconductors are either insoluble in common organic solvents or sensitive to air, and are therefore not suitable for fabricating low-cost OTFTs via liquid patterning and deposition processes under ambient conditions. There is therefore a critical need addressed by embodiments of the present invention to develop liquid-processable and air stable organic semiconductor compounds to enable low-cost OTFTs.

The following documents provide background information:

Christos D. Dimitrakopoulos et al., "Organic Thin Film Transistors for Large Area Electronics," Adv. Mater., Vol. 14, No. 2, pp. 99-117 (2002).

Salem Wakim et al., "Organic Microelectronics: Design, Synthesis, and Characterization of 6,12-Dimethylindolo[3,2-b]Carbazoles," Chem. Mater. Vol. 16, No. 23, pp. 4386-4388 (published on web Jul. 7, 2004).

Nan-Xing Hu et al., "5-11-Dihydro-5,11-di-1-naphthylindolo[3,2-b]carbazole: Atropisomerism in a Novel Hole-Transport Molecule for Organic Light-Emitting Diodes," J. Am. Chem. Soc., Vol. 121, pp. 5097-5098 (1999).

Ong et al., U.S. Pat. No. 6,949,762
Hu et al., U.S. Pat. No. 5,942,340.
Hu et al., U.S. Pat. No. 5,952,115.
Hu et al., U.S. Pat. No. 5,843,607.

SUMMARY OF THE DISCLOSURE

In embodiments, there is provided a compound comprising at least one type of an optionally substituted indolocarbazole moiety and at least one divalent linkage.

In further embodiments, there is provided a small molecule compound comprising at least one type of an optionally substituted indolocarbazole moiety and at least one divalent linkage.

In other embodiments, there is provided a polymer comprising at least one type of repeat unit comprising at least one type of an optionally substituted indolocarbazole moiety and at least one divalent linkage.

In embodiments, there is provided an electronic device comprising a compound comprising at least one type of an optionally substituted indolocarbazole moiety and at least one divalent linkage.

In further embodiments, there is provided an electronic device comprising a small molecule compound comprising at least one type of an optionally substituted indolocarbazole moiety and at least one divalent linkage.

In other embodiments, there is provided an electronic device comprising a polymer comprising at least one type of repeat unit comprising at least one type of an optionally substituted indolocarbazole moiety and at least one divalent linkage.

BRIEF DESCRIPTION OF THE DRAWINGS

Other aspects of the present invention will become apparent as the following description proceeds and upon reference to the following figures which are representative embodiments.

Unless otherwise noted, the same reference numeral in different Figures refers to the same or similar feature.

DETAILED DESCRIPTION

Figure 1:
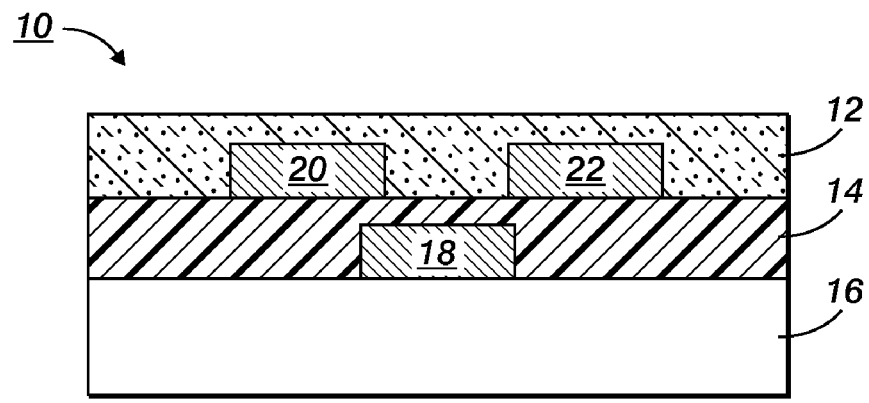
FIG. 1 represents a first embodiment of the present invention in the form of an OTFT.

The present compound ("Compound") encompasses polymers and small molecule compounds. As used herein, a "polymer" includes one, two, or more types of repeat units. In embodiments of the "polymer," each type of repeat unit has any suitable number of repeat units ranging for example from 2 to about 2000, or from about 5 to about 1000. In embodiments of the "polymer," the number of repeat units regardless of type (that is, for all types) ranges for example from 2 to about 2000, or from about 5 to about 1000. An "oligomer" is a subset of a "polymer" having a small number of repeat units where the "oligomer" may be for example a dimer, trimer, and the like.

The repeat unit is the fundamental recurring unit of a polymer. The connection of the repeat units in the polymer may be identical, In the case of a regular polymer, or may be not identical, in the case of an irregular polymer, with respect to directional sense. Whether a repeat unit A is considered the same type or a different type as another repeat unit B is independent of directional sense when repeat unit A and repeat unit B are in the polymer. For instance, regiorandom poly(3-hexyl thiophene) is considered to have only one type of repeat unit. As another example, Xinnan Zhang et al., "Alkyl-Substituted Thieno[3,2-b] thiophene Polymers and Their Dimeric Subunits," *Macromolecules*, Vol. 37, pp. 6306-6315 (published on web Jul. 30, 2004), discloses a regiorandom poly(3-alkylthieno[3,2-b]thiophene) which is considered to have only one type of repeat unit.

As used herein, the phrase "small molecule compound" refers to a compound without a repeat unit regardless of its molecular weight. Thus, a compound having a low, medium, or high molecular weight but without a repeat unit would be considered a "small molecule compound" for the present purposes.

In embodiments, the Compound is a molecular compound. The phrase "molecular compound" refers to any "polymer" and "small molecule compound" having a specific molecular weight rather than an average molecular weight. While a "small molecule compound" is generally also a "molecular compound" with a specific molecular weight, a "polymer" can have an average molecular weight or a specific molecular weight depending on whether the "polymer" has predominantly molecules with the same number of repeat units (resulting in a specific molecular weight) or a mixture of molecules with different numbers of repeat units (resulting in an average molecular weight).

In the Compound, there is one type, two types, three types, or more of the optionally substituted indolocarbazole moiety and of the divalent linkage. Dissimilarity in any manner can create different "types". For example, a difference in any one or more of the following representative factors creates different "types" of the indolocarbazole moiety and of the divalent linkage in the Compound: (a) whether there is substitution; (b) the type, position and/or number of substituent(s); and (c) the type of the indolocarbazole for example the illustrative structures A to G as shown thereafter.

The phrase "at least one divalent linkage" refers to the divalent linkage(s) without regard to type. There can be one, two, or more types of divalent linkage(s) present in the Compound.

In embodiments, the Compound includes a number of the optionally substituted indolocarbazole moiety regardless of type ranging for example from 2 to 1000 and a number of the at least one divalent linkage regardless of type ranging for example from 1 to 500. In embodiments, each type of the optionally substituted indolocarbazole moiety includes a number of indolocarbazole moiety ranging for example from 1 to 1000. In embodiments, each type of the divalent linkage includes a number of the divalent linkage ranging for example from 1 to 500. In embodiments where the Compound is a small molecule compound, the number of the optionally substituted indolocarbazole moiety regardless of type ranges for example from 2 to 30 or from 2 to 10; and the number of the at least one divalent linkage regardless of type ranges for example from 1 to 15 or from 1 to 5. In embodiments where the Compound is a polymer, the number of the optionally substituted indolocarbazole moiety ranges for example from 1 to 6 for each type of the repeat unit; and the number of the at least one divalent linkage ranges for example from 1 to 3 for each type of the repeat unit.

The indolocarbazole moiety of the Compound is unsubstituted or substituted with one or more substituents in any suitable substitution pattern. For substituted embodiments of the indolocarbazole moiety, the substitution can be for example the following: (1) one or more nitrogen substitutions (that is, substitution(s) at the nitrogen atoms) with no peripheral substitution; (2) one or more peripheral substitutions with no nitrogen substitution; or (3) one or more nitrogen substitutions and one or more peripheral substitutions. In embodiments, all the nitrogen atoms of the indolocarbazole moiety are substituted with the same or different substituents, with the indolocarbazole moiety being optionally peripherally substituted. In embodiments, the indolocarbazole moiety is nitrogen substituted (and optionally peripherally substituted) wherein the one or more nitrogen substituents are independently selected from the group consisting of a hydrocarbon group and a heteroatom-containing group, or a mixture thereof. In embodiments, the indolocarbazole moiety is peripherally substituted (and optionally nitrogen substituted) wherein the one or more peripheral substituents are independently selected from the group consisting of a hydrocarbon group, a heteroatom-containing group, and a halogen, or a mixture thereof.

The phrases "peripherally substituted" and "peripheral substitution" refer to at least one substitution (by the same or different substituents) on any one or more aromatic rings of the indolocarbazole moiety regardless whether the aromatic ring is a terminal aromatic ring or an internal aromatic ring (that is, other than at a terminal position).

In embodiments, the indolocarbazole moieties of the Compound are independently selected from the group consisting of structures (A), (B), (C), (D), (E), (F), and (G), or a mixture thereof.

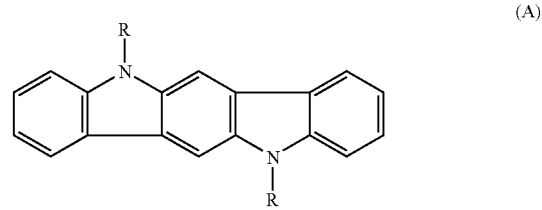

(A)

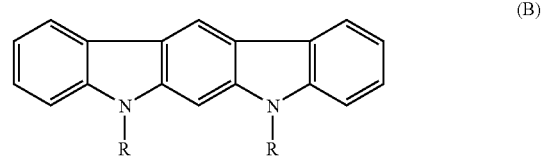

(B)

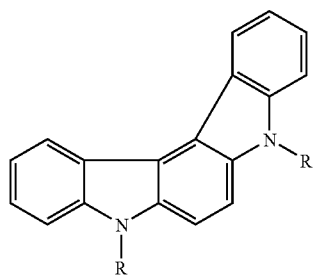

(C)

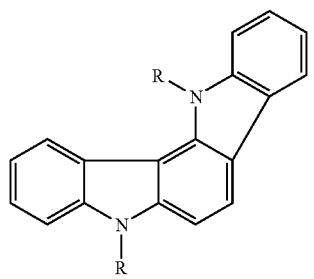

(D)

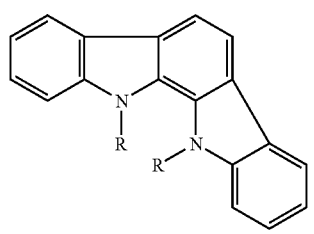

(E)

(F)

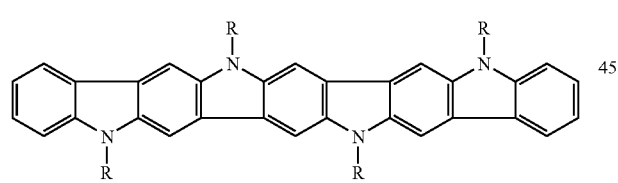

(G)

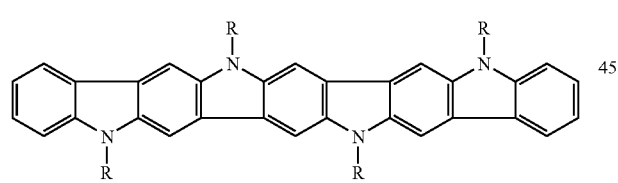

wherein for each of the structures (A) through (G), each R is independently selected from a group consisting of a hydrogen, a hydrocarbon group and a heteroatom-containing group (that is, each nitrogen atom can have the same or different R), wherein each of the structures (A) through (G) is optionally peripherally substituted by one or more substituents selected from the group consisting of a hydrocarbon group, a heteroatom-containing group, and a halogen, or a mixture thereof.

In embodiments, each divalent linkage is "conjugated" or "non-conjugated" which indicates the nature of the backbone structure(s); it is understood that any optional substituent(s) on the backbone structure(s) may or may not be "conjugated." Representative examples of a "non-conjugated" divalent linkage include an oxygen atom and an alkylene containing for instance one to about ten carbon atoms. In embodiments, each divalent linkage may be selected for example from the group consisting of the following structural units which are optionally substituted:

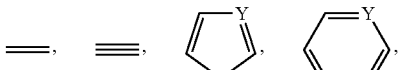

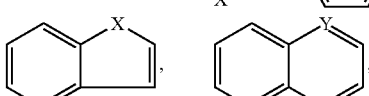

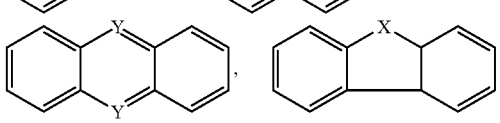

and a combination thereof ("combination" referring to coupling of two or more of the depicted structures such as for instance the double bond structure coupled to any of the aromatic structures), wherein X is selected from the group consisting of C(R'R"), O, S, Se, NR', and Si(R'R"), and wherein R' and R" are independently selected from the group consisting of a hydrocarbon group, a heteroatom-containing group, a halogen and a mixture thereof; and Y is a carbon atom or a nitrogen atom.

Each divalent linkage is unsubstituted or substituted with one or more substituents in any suitable substitution pattern. For substituted embodiments of the divalent linkage(s), the substituent(s) can be independently selected from the group consisting of a hydrocarbon group, a heteroatom-containing group, a halogen and a mixture thereof.

In embodiments, each divalent linkage comprises one, two, or more optionally substituted thienylene units, each thienylene unit being the same or different from each other and of representative structure (I)

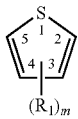

(I)

where $R_1$ is independently selected from a hydrocarbon group (such as those described herein for the optionally substituted indolocarbazole moiety), a heteroatom-containing group (such as those described herein for the optionally substituted indolocarbazole moiety), and a halogen, and where m is 0, 1, or 2. Covalent bondings to other part or moieties of the Compound are not shown in structure (I). It is understood that each thienylene unit will have covalent bondings, preferably at 2 and 5 positions, when incorporated into the Compound.

A divalent linkage is different from a substituent of the indolocarbazole moiety. Substituents are bonded to the indolocarbazole moiety via a single covalent bond. On the other hand, the divalent linkage is bonded in a divalent manner at two positions to for instance two indolocarbazole moieties. For example, the bithienylene between the two indolocarbazole moieties is considered as the divalent linkage of the Compound (1), while the 5-hexyl-thienyl groups at both ends of the Compound (1) are considered as substituents of the indolocarbazole moiety. Similarly, the biphenylene in the repeat unit of the polymer (17) is considered as the divalent linkage ("biphenylene" for polymer 17 refers to the two phenylene moieties between adjacent indolocarbazole moieties; thus, in the repeat unit for polymer (17), two biphenylenes are coupled to the indolocarbazole moiety but only one phenylene moiety of each biphenylene is depicted), while the 4-octylphenyl groups at the nitrogen positions are considered as substituents of the indolocarbazole moiety. For Compound (1) and Compound (17), the biphenylene could also be viewed as two divalent linkages rather than a single divalent linkage. In embodiments, it is generally immaterial whether to view the biphenylene as a single divalent linkage or two divalent linkages. In embodiments, however, one can consider the moieties at issue to be a single divalent linkage if the chemical nomenclature indicates such a view is appropriate. In embodiments, one can consider all the moieties between adjacent indolocarbazole moieties to be a single divalent linkage, particularly for instance when the present claims recite "only one divalent linkage."

an alkoxyaryl, an arylalkoxy, and a halogenated hydrocarbon (where the halogen is for example fluorine, bromine, chlorine, or iodine, or a mixture thereof). Representative heteroatom-containing groups include for example fluoroalkyl, fluoroaryl, cyano, nitro, carbonyl, carboxylate, amino (optionally substituted with one or two substituents such as for example a hydrocarbon group described herein), and alkoxy (having for example 1 to about 18 carbon atoms). In embodiments, the heteroatom-containing group is independently selected from the group consisting of fluoroalkyl (having for example 1 to about 18 carbon atoms), fluoroaryl, cyano, nitro, carbonyl, carboxylate, alkoxy (having for example 1 to about 18 carbon atoms), and amino (optionally substituted with one or two substituents such as for example a hydrocarbon group described herein), or a mixture thereof. In embodiments, the heteroatom-containing group is an optionally substituted carbazole group.

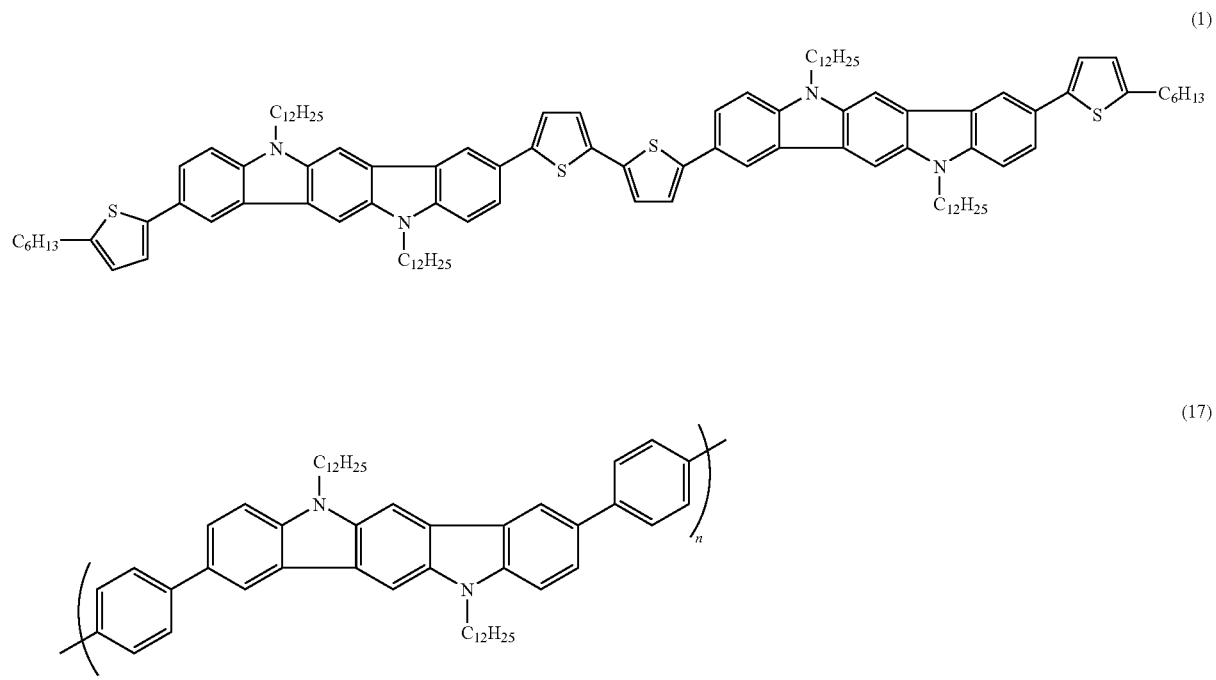

The hydrocarbon group of the optional substituent(s) for the Compound (both the optional substituent(s) of the indolocarbaozle moiety and the optional substituent(s) of the divalent linkage) contains for example from 1 to about 50 carbon atoms, or from 1 to about 30 carbon atoms, and may be for example a straight chain alkyl group, a branched alkyl group, a cyclic aliphatic group, an aryl group, an alkylaryl group, and an arylalkyl group. Representative hydrocarbon groups include for example methyl, ethyl, propyl, butyl, pentyl, hexyl, heptyl, octyl, nonyl, decyl, undecyl, dodecyl, tridecyl, tetradecyl, pentadecyl, cyclopentyl, cyclohexyl, cycloheptyl, and isomeric forms thereof.

The heteroatom-containing group of the optional substituent(s) for the Compound (both the optional substituent(s) of the indolocarbaozle moiety and the optional substituent(s) of the divalent linkage) has for example 2 to about 200 atoms, or from 2 to about 100 atoms) and may be for example a nitrogen-containing group, an alkoxy group, a heterocyclic group, The halogen of the optional substituent(s) for the Compound (both the optional substituent(s) of the indolocarbaozle moiety and the optional substitutent(s) of the divalent linkage) is for example fluorine, bromine, chlorine, or iodine, or a mixture thereof).

The Compound may be a p-type semiconductor, n-type semiconductor or ambipolar semiconductor. The type of the semiconducting of the Compound depends very much on the nature of the substituents. Substituents which possess an electron donating property such as alkyl, alkoxy, aryl, and amino groups, when present in the Compound, may render the Compound a p-type semiconductor. On the other hand, substituents which are electron withdrawing such as cyano, nitro, fluoro, fluorinated alkyl, and fluorinated aryl groups may transform the Compound into the n-type semiconductor.

Illustrative embodiments of the Compound (involving small molecule compounds) are:

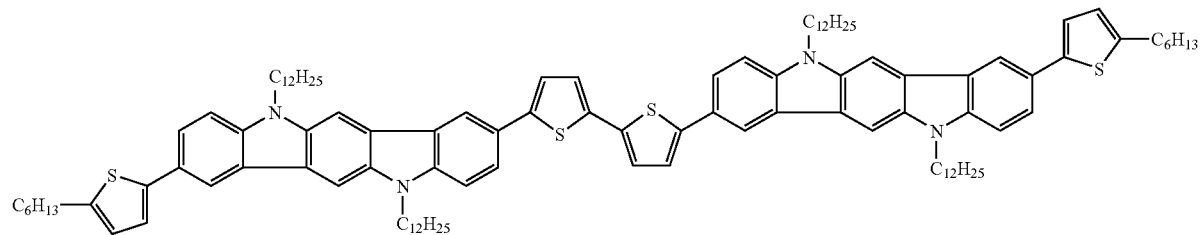
(1)
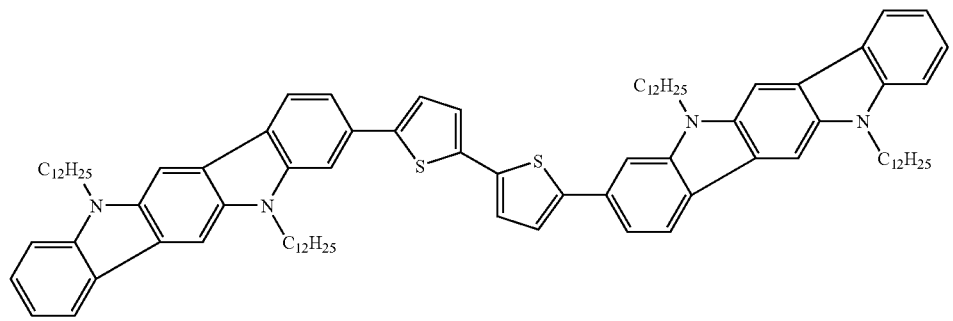
(2)
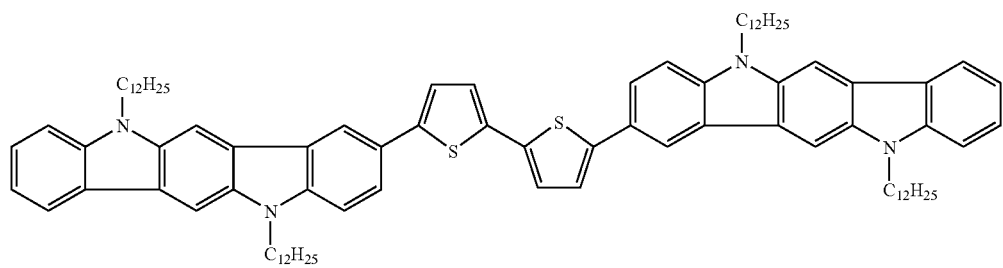
(3)
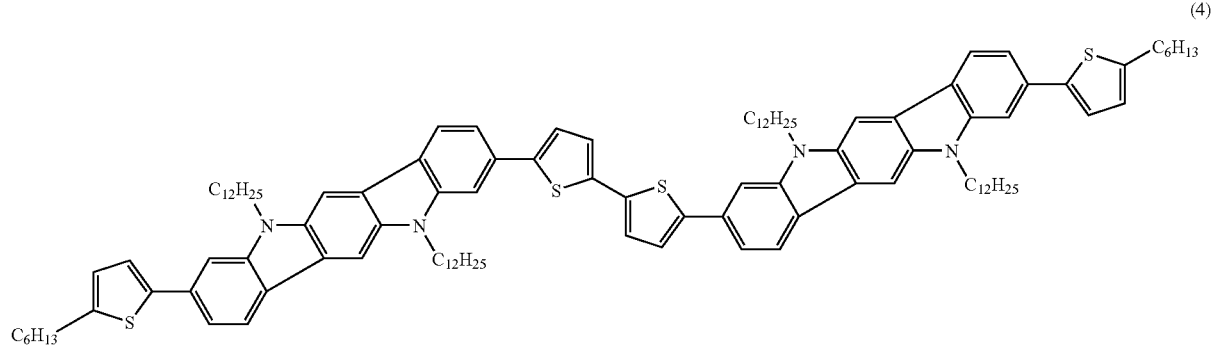
(4)
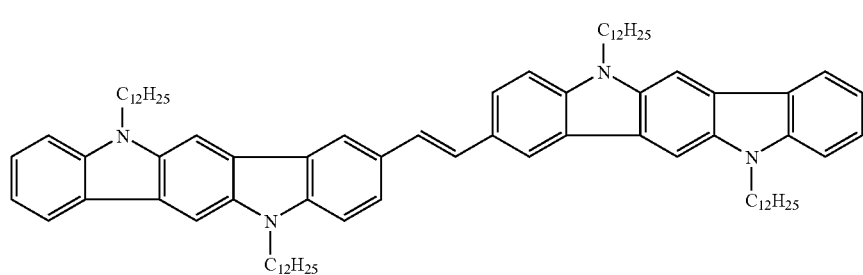
(5)

-continued
(6)
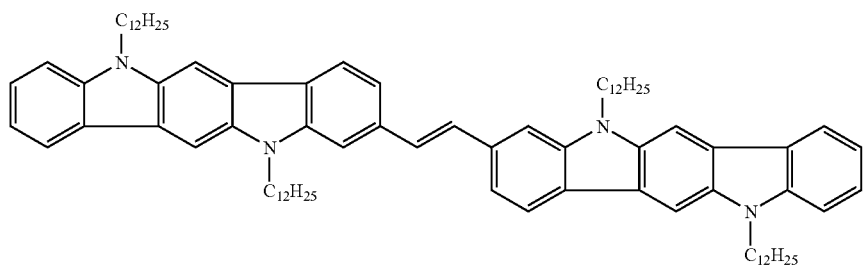
(7)
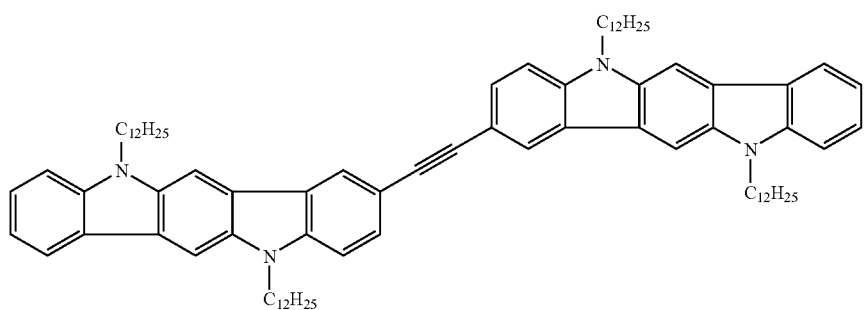
(8)
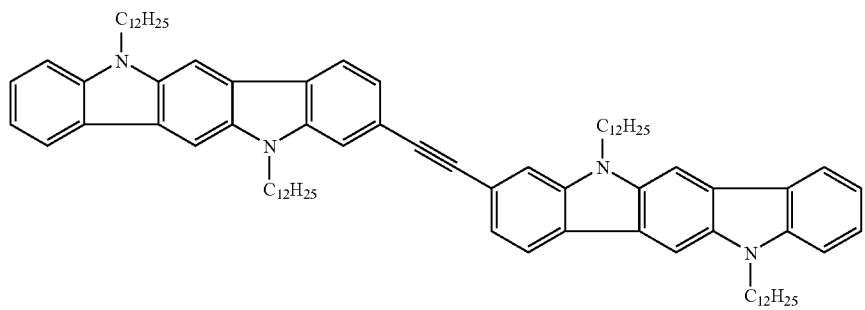
(9)
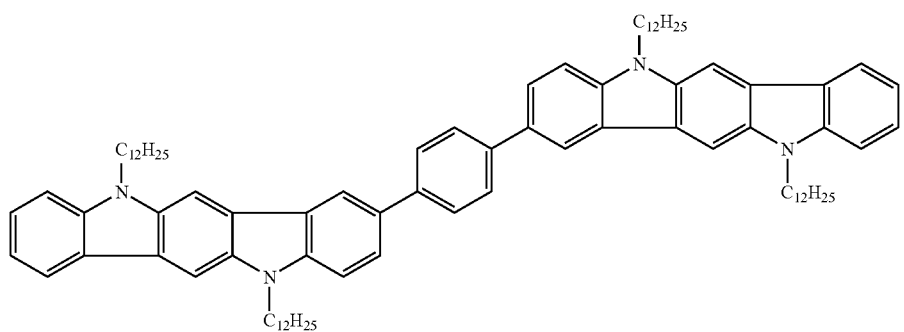
(10)
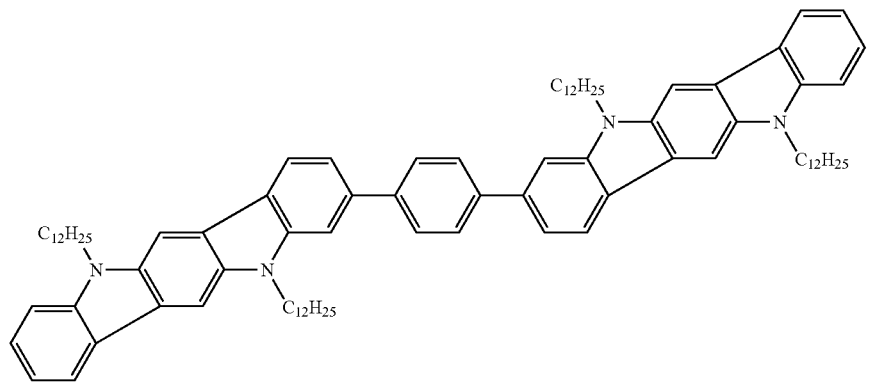

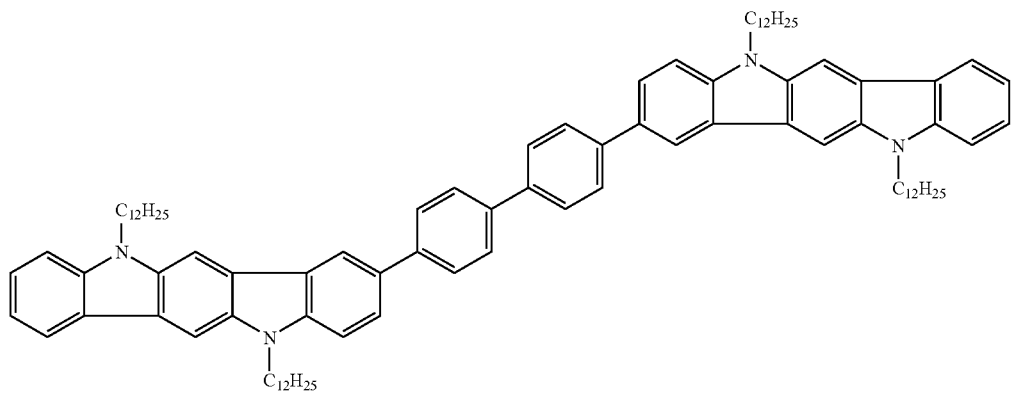
(11)
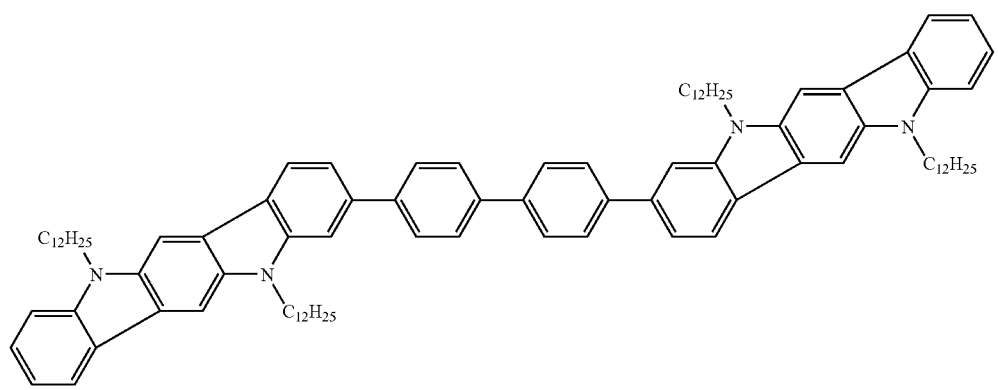
(12)
Further embodiments of the Compound (involving polymers) are:
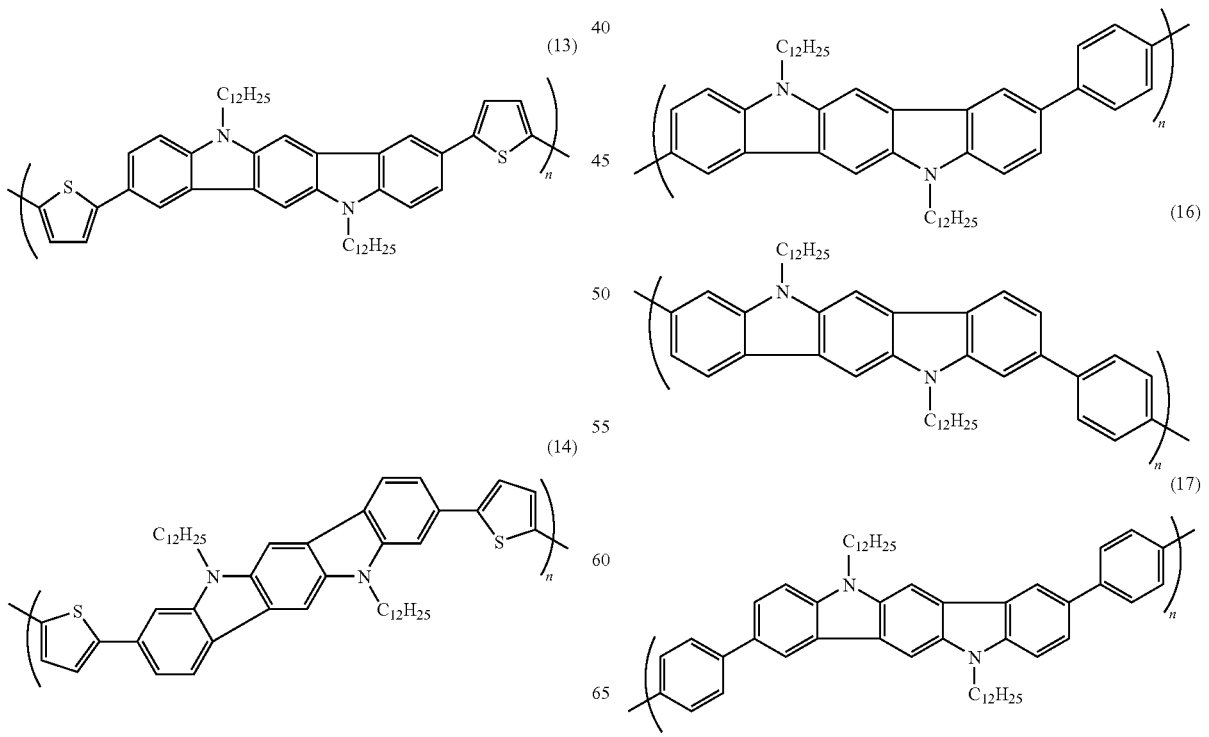
(13)
(14)
(15)
(16)
(17)

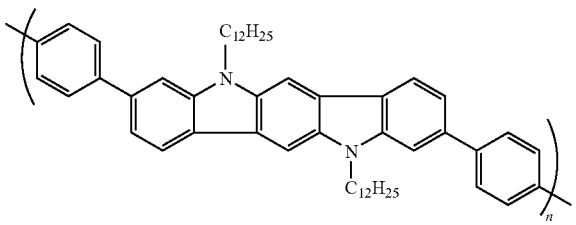

(18)

where n ranges for example from 2 to about 2000.

The Compound can be prepared for instance by an appropriate coupling reaction of an optionally substituted indolocarbazole (a single optionally substituted indolocarbazole or a mixture of two or more different optionally substituted indolocarbazoles in any suitable ratios) with a divalent linkage precursor (e.g., dibronic acids in Schemes 1 and 2). For example, Compound (1), (2), and (9) through (12) can be synthesized via Suzuki coupling reaction of 2- or 3-bromo-5,11-didodecylinodolo[3,2-b]carbazole with diboronic acids as shown in Scheme 1.

Scheme 1. Synthesis of Compound (1), (2), and (9) through (12).

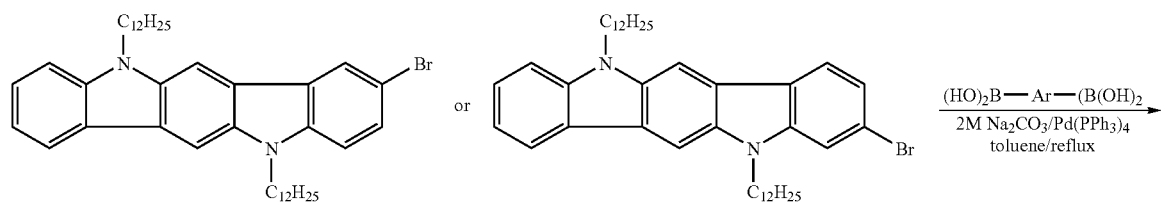

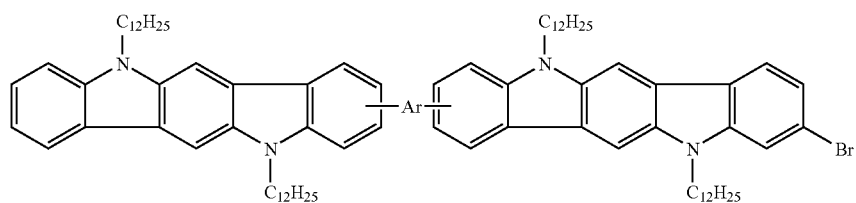

Ar:

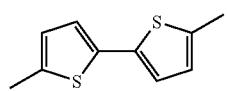 (1)/(2)

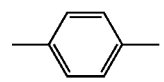 (9)/(10)

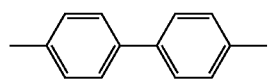 (11)/(12)

In embodiments, a polymeric Compound can be, for example, prepared by copolymerizing a difunctional monomer comprising an optionally substituted indolocarbazole with divalent linkage precursor (e.g., a difunctional monomer comprising an unsaturated compound) or polymerizing of appropriate functionalized monomer of an optionally substituted indolocarbazole (the functionalized monomer is functionalized with a divalent linkage precursor) as represented in Schemes 2 and 3 respectively. For example, polymer (13) through (18) can be prepared via Suzuki coupling polymerization of 3,9- or 2,8-dibromo-5,11-didodecylindolo[3,2-b]carbazole with diboronic acids (Scheme 2). Alternatively, polymer (13) can be prepared via oxidative coupling polymerization of 2,8-bis(2-thienyl)-5,11-didodecylindolo[3,2-b]carbazole with $FeCl_3$ (Scheme 3).

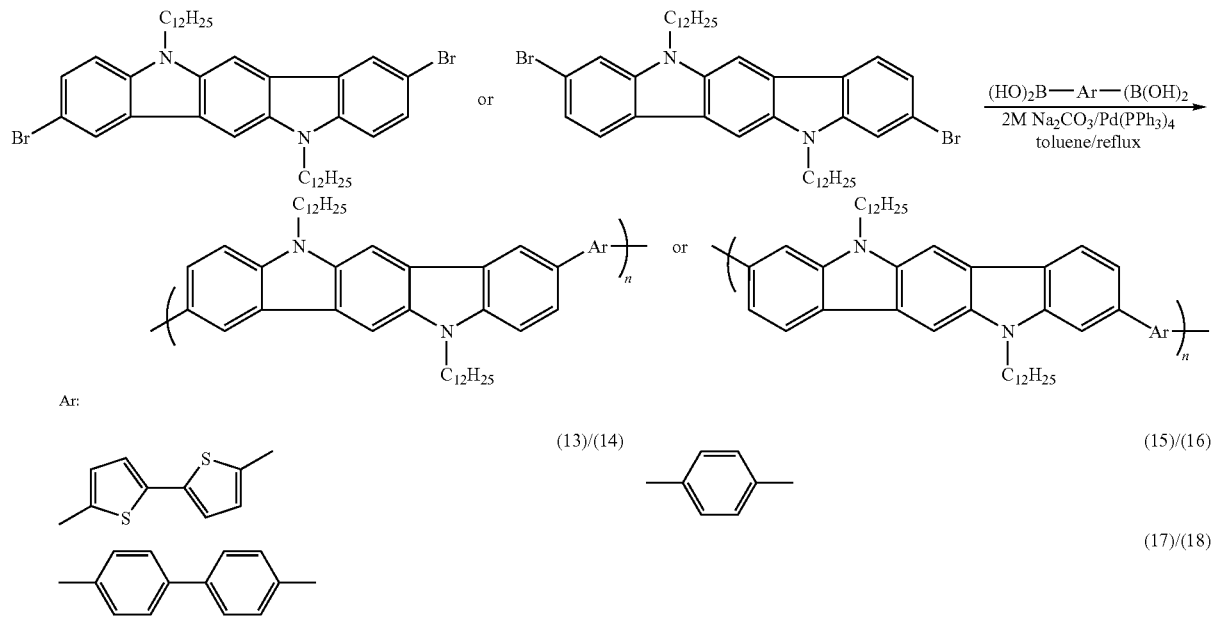

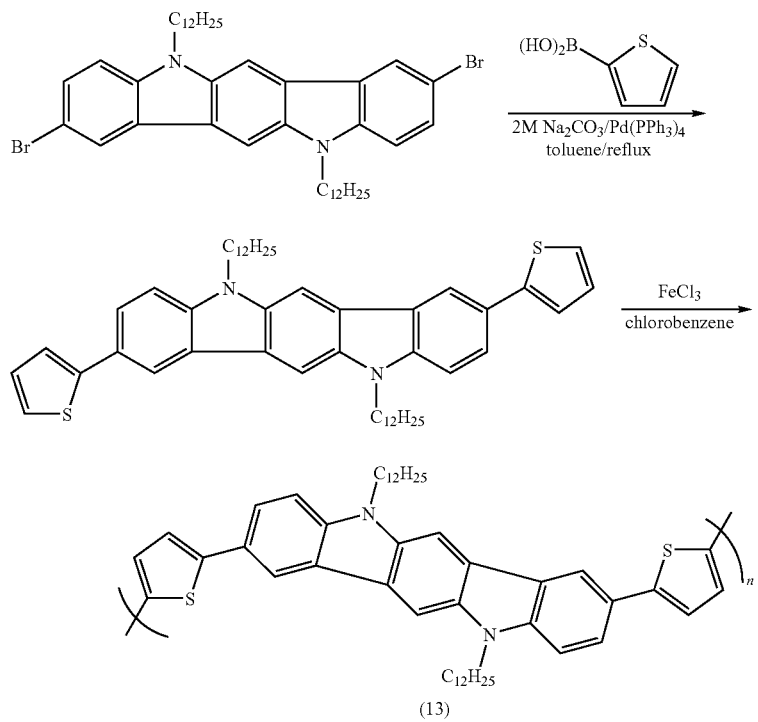

The Compound may be used for any suitable applications. In embodiments, the Compound may be used as a semiconductor for electronic devices such as for example diodes, thin film transistors, and photovoltaics.

Any suitable techniques may be used to form a semiconductor layer containing the Compound. One such method for small molecular compounds is by vacuum evaporation at a vacuum pressure of about $10^{-5}$ to $10^{-7}$ torr in a chamber containing a substrate and a source vessel that holds the Compound in powdered form. Heat the vessel until the Compound sublimes onto the substrate. The performance of the films containing the Compound may depend on the rate of heating, the maximum source temperature and substrate temperature during the evaporation process. In embodiments, liquid deposition techniques may also be used to fabricate the semiconductor layer comprised of the Compound, particularly the polymeric compounds. Liquid deposition techniques refer to for example spin coating, blade coating, rod coating, screen printing, ink jet printing, stamping and the like. Specifically, the Compound can be dissolved in a suitable solvent of for example tetrahydrofuran, dichloromethane, chlorobenzene, toluene, and xylene to form a solution at a concentration of about 0.1% to about 10%, particularly about 0.5% to about 5% by weight, and then used in liquid deposition. Illustrative deposition by spin coating can be carried out at a spin speed of about 500 to about 3000 rpm, particularly about 1000 to about 2000 rpm for a period of time of about 5 to about 100 seconds, particularly about 30 to about 60 seconds at room temperature or an elevated temperature to form a thin film on a suitable substrate such as silicon wafer, glass, or plastic film.

The semiconductor layer may be predominantly amorphous, liquid crystalline or predominantly crystalline in nature, depending on the Compound and processing conditions. The semiconductor layer can be characterized by common characterization techniques such as X-ray diffraction, atomic force microscopy, optical microscopy, etc. For example, a predominantly amorphous layer usually shows broad X-ray diffraction peaks, while a predominantly crystalline layer generally exhibits sharp X-ray diffraction peaks. The degree of crystallinity of a semiconductor layer can be calculated from the integrated area of diffraction peaks. In embodiments, the phrase "predominately crystalline" indicates that the crystallinity of the semiconductor layer is for example larger than about 50%, larger than about 80%, or larger than about 90%.

Depending on the nature of the Compound, a predominantly crystalline semiconductor layer can be formed by a number of techniques. For example, a predominantly crystalline semiconductor layer can be formed by vacuum evaporation of the Compound onto a substrate holding at an elevated temperature of for example about 50° C. to about 120° C. In another technique, a predominantly crystalline semiconductor layer can be achieved by liquid deposition followed by controlled solvent evaporation and optionally post-deposition annealing at an elevated temperature of for example about 80° C. to about 250° C.

The representative use of Compound as a semiconductor in electronic devices is illustrated herein using thin film transistors.

In FIG. 1, there is schematically illustrated an OTFT configuration 10 comprised of a substrate 16, in contact therewith a metal contact 18 (gate electrode) and a layer of a gate dielectric layer 14 on top of which two metal contacts, source electrode 20 and drain electrode 22, are deposited. Over and between the metal contacts 20 and 22 is an organic semiconductor layer 12 as illustrated herein.

Figure 2:
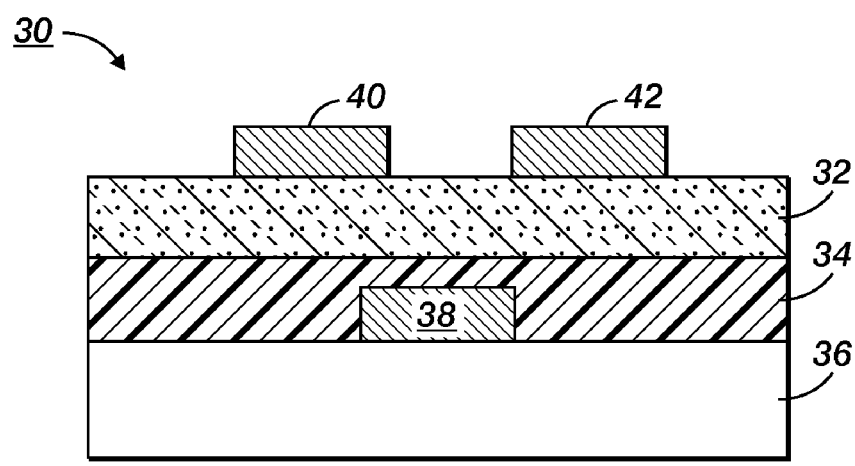
FIG. 2 represents a second embodiment of the present invention in the form of an OTFT.

FIG. 2 schematically illustrates another OTFT configuration 30 comprised of a substrate 36, a gate electrode 38, a source electrode 40 and a drain electrode 42, a gate dielectric layer 34, and an organic semiconductor layer 32.

Figure 3:
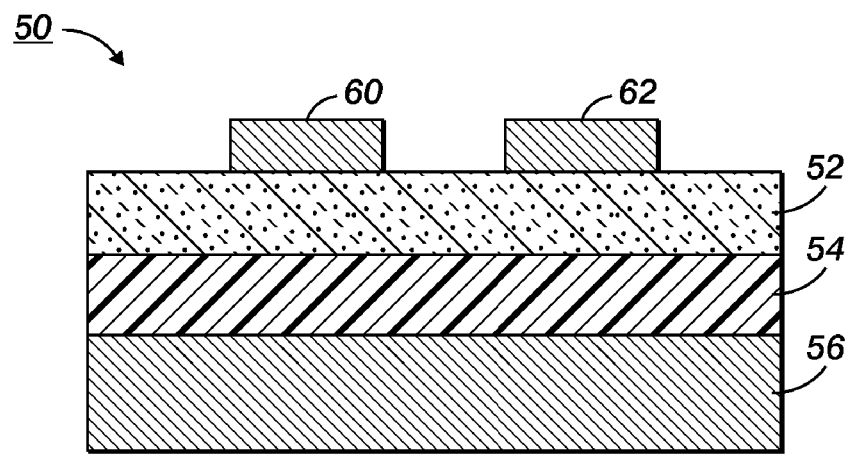
FIG. 3 represents a third embodiment of the present invention in the form of an OTFT.

FIG. 3 schematically illustrates a further OTFT configuration 50 comprised of a heavily n-doped silicon wafer 56 which acts as both a substrate and a gate electrode, a thermally grown silicon oxide gate dielectric layer 54, and an organic semiconductor layer 52, on top of which are deposited a source electrode 60 and a drain electrode 62.

Figure 4:
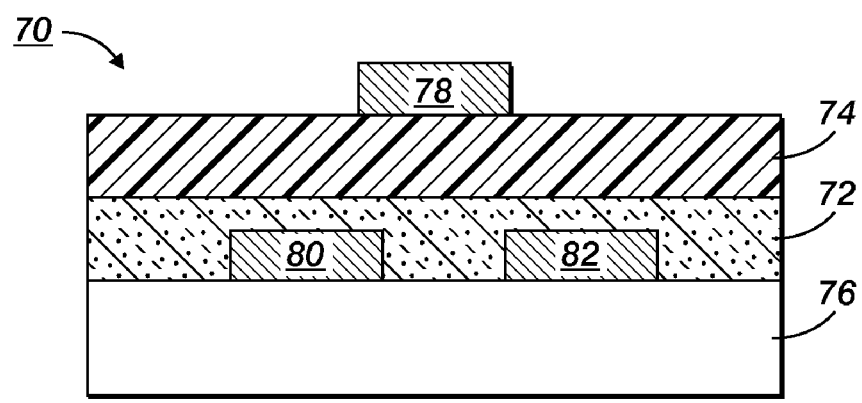
FIG. 4 represents a fourth embodiment of the present invention in the form of an OTFT.

FIG. 4 schematically illustrates an additional OTFT configuration 70 comprised of substrate 76, a gate electrode 78, a source electrode 80, a drain electrode 82, an organic semiconductor layer 72, and a gate dielectric layer 74.

The composition and formation of the semiconductor layer are described herein.

The semiconductor layer has a thickness ranging for example from about 10 nanometers to about 1 micrometer with a preferred thickness of from about 20 to about 200 nanometers. The OTFT devices contain a semiconductor channel with a width W and length L. The semiconductor channel width may be, for example, from about 1 micrometers to about 5 millimeters, with a specific channel width being about 5 micrometers to about 1 millimeter. The semiconductor channel length may be, for example, from about 1 micrometer to about 1 millimeter with a more specific channel length being from about 5 micrometers to about 100 micrometers.

The substrate may be composed of for instance silicon, glass plate, plastic film or sheet. For structurally flexible devices, a plastic substrate, such as for example polyester, polycarbonate, polyimide sheets and the like may be preferred. The thickness of the substrate may be from about 10 micrometers to over about 10 millimeters with an representative thickness being from about 50 to about 100 micrometers, especially for a flexible plastic substrate and from about 1 to about 10 millimeters for a rigid substrate such as glass plate or silicon wafer.

The gate electrode can be a thin metal film, a conducting polymer film, a conducting film made from conducting ink or paste, or the substrate itself can be the gate electrode, for example heavily doped silicon. Examples of gate electrode materials include but are not restricted to aluminum, gold, chromium, indium tin oxide, conducting polymers such as polystyrene sulfonate-doped poly(3,4-ethylenedioxythiophene) (PSS-PEDOT), conducting ink/paste comprised of carbon black/graphite or colloidal silver dispersion in polymer binders, such as ELECTRODAG™ available from Acheson Colloids Company. The gate electrode layer can be prepared by vacuum evaporation, sputtering of metals or conductive metal oxides, coating from conducting polymer solutions or conducting inks by spin coating, casting or printing. The thickness of the gate electrode layer ranges for example from about 10 to about 200 nanometers for metal films and in the range of about 1 to about 10 micrometers for polymer conductors.

The source and drain electrode layers can be fabricated from materials which provide a low resistance ohmic contact to the semiconductor layer. Typical materials suitable for use as source and drain electrodes include those of the gate electrode materials such as gold, nickel, aluminum, platinum, conducting polymers and conducting inks. Typical thicknesses of source and drain electrodes are about, for example, from about 40 nanometers to about 10 micrometers with the more specific thickness being about 100 to about 400 nanometers.

The gate dielectric layer generally can be an inorganic material film or an organic polymer film. Illustrative examples of inorganic materials suitable as the gate dielectric layer include silicon oxide, silicon nitride, aluminum oxide, barium titanate, barium zirconium titanate and the like; illustrative examples of organic polymers for the gate dielectric layer include polyesters, polycarbonates, poly(vinyl phenol), polyimides, polystyrene, poly(methacrylate)s, poly(acrylate)s, epoxy resin and the like. The thickness of the gate dielectric layer is, for example from about 10 nanometers to about 500 nanometers depending on the dielectric constant of the dielectric material used. An representative thickness of the gate dielectric layer is from about 100 nanometers to about 500 nanometers. The gate dielectric layer may have a conductivity that is for example less than about $10^{-12}$ S/cm.

The gate dielectric layer, the gate electrode, the semiconductor layer, the source electrode, and the drain electrode are formed in any sequence with in embodiments the gate electrode and the semiconductor layer both contacting the gate dielectric layer, and the source electrode and the drain electrode both contacting the semiconductor layer. The phrase "in any sequence" includes sequential and simultaneous formation. For example, the source electrode and the drain electrode can be formed simultaneously or sequentially. The composition, fabrication, and operation of field effect transistors are described in Bao et al., U.S. Pat. No. 6,107,117, the disclosure of which is totally incorporated herein by reference.

For a p-channel OTFT, the source electrode is grounded and a bias voltage of generally, for example, about 0 volt to about −80 volts is applied to the drain electrode to collect the charge carriers transported across the semiconductor channel when a voltage of generally about +20 volts to about −80 volts is applied to the gate electrode.

The semiconductor layer comprising the Compound in an OTFT device generally exhibit a field-effect mobility of greater than for example about $10^{-3}$ cm$^2$/Vs (square centimeter per Volt per second), and an on/off ratio of greater than for example about $10^3$. On/off ratio refers to the ratio of the source-drain current when the transistor is on to the source-drain current when the transistor is off.

The invention will now be described in detail with respect to specific representative embodiments thereof, it being understood that these examples are intended to be illustrative only and the invention is not intended to be limited to the materials, conditions, or process parameters recited herein. All percentages and parts are by weight unless otherwise indicated. As used herein, room temperature refers to a temperature ranging for example from about 20 to about 25 degrees C.

EXAMPLE 1

Synthesis and Properties of Polymer (13)

(a) 2,8-Bis(2-thienyl)-5,11-didodecylindolo[3,2-b]carbazole (Scheme 3)

ALIQUAT™336 (0.6 g), 2-thiopheneboronic acid (0.921 g, 7.2 mmol), 2,8-dibromo-5,11-didodecylindolo[3,2-b]carbazole (2.252 g, 3 mmol), 2M Na$_2$CO$_3$ solution (7.5 mL, 15 mmol), Pd(PPh$_3$)$_4$ (72 mg, 0.06 mmol) and toluene (10 mL) were added into a 50 mL flask. The mixture was heated to gentle reflux and maintained for 48 h. The reaction mixture was cooled down, organic layer separated, dried, and filtered. The toluene solution was passed through a silica gel column and the solvent was removed. Recrystallization from toluene gave the title compound as a yellow solid. Yield: 1.476 g (61%).

(b) Polymer (13) (Scheme 3)

FeCl$_3$ (0.45 g, 2.77 mmol) and chlorobenzene (10 mL) were added to the flask and protected by argon. 2,8-bis(2-thienyl)-5,11-didodecylindolo[3,2-b]carbazole (0.50 g, 0.66 mmol) in chlorobenzene (10 mL) was added dropwise to above solution. The reaction mixture was stirred at for 24 h and then poured into methanol (100 mL). The solid was filtered off and washed with water and methanol. The solid was stirred in ammonia solution for 24 h. The solid was washed off and washed with water and methanol. The solid was collected in the thimble and was subjected to Soxhlet extraction with heptane for 24 h. The polymer was then dissolved by refluxing chlorobenzene. The solution was concentrated and added to methanol to afford a solid polymer, which was dried under a reduced pressure. Yield: 0.114 g (23%).

(c) OTFT Fabrication and Characterization

A top-contact thin film transistor configuration as schematically illustrated, for example, in FIG. 3 was selected as our test device structure. The test device was built on an n-doped silicon wafer with a thermally grown silicon oxide layer with a thickness of about 110 nanometers thereon, and had a capacitance of about 30 nF/cm$^2$ (nanofarads/square centimeter), as measured with a capacitor meter. The wafer functioned as the gate electrode while the silicon oxide layer acted as the gate dielectric. The silicon wafer was first cleaned with isopropanol, argon plasma, isopropanol and air dried, and then immersed in a 0.1 M solution of octyltrichlorosilane (OTS-8) in toluene at 60° C. for 20 min. Subsequently, the wafer was washed with toluene, isopropanol and air-dried. A solution of polymer (13) dissolved in chlorobenzene (0.5 percent by weight) was first filtered through a 1.0 micrometer syringe filter, and then spin-coated on the OTS-8-treatet silicon wafer at 1000 rpm for 60 seconds at room temperature. This resulted in the formation of a semiconductor layer with a thickness of 20-50 nanometers on the silicon wafer, which was then dried in a vacuum oven at 80° C. for 5-10 h. Subsequently, gold source and drain electrodes of about 50 nanometers in thickness were deposited on top of the semiconductor layer by vacuum deposition through a shadow mask with various channel lengths and widths, thus creating a series of transistors of various dimensions.

The evaluation of transistor performance was accomplished in a black box (that is, a closed box which excluded ambient light) at ambient conditions using a Keithley 4200 SCS semiconductor characterization system. The carrier mobility, μ, was calculated from the data in the saturated regime (gate voltage, $V_G$<source-drain voltage, $V_{SD}$) according to equation (1)

$$I_{SD}=C_i\mu(W/2L)(V_G-V_T)^2 \qquad (1)$$

where $I_{SD}$ is the drain current at the saturated regime, W and L are, respectively, the semiconductor channel width and length, $C_i$ is the capacitance per unit area of the gate dielectric layer, and $V_G$ and $V_T$ are, respectively, the gate voltage and threshold voltage. $V_T$ of the device was determined from the relationship between the square root of $I_{SD}$ at the saturated regime and $V_G$ of the device by extrapolating the measured data to $I_{SD}$=0.

The transfer and output characteristics of the devices showed that compound was a p-type semiconductor. Using transistors with a dimension of W=5,000 μm and L=90 μm, the following average properties from at least five transistors were obtained:

Mobility: $1.0 \times 10^{-3}$ cm$^2$/V·s

On/off ratio: $10^5$.

The mobility and current on/off ratio achieved by embodiments of the present thin film transistor devices are useful for various applications in electronics such as for example electronic paper.

What is claimed is:

1. A small molecule compound consisting of at least one type of an indolocarbazole moiety and at least one divalent linkage,
   wherein the at least one divalent linkage is independently selected from the group consisting of:

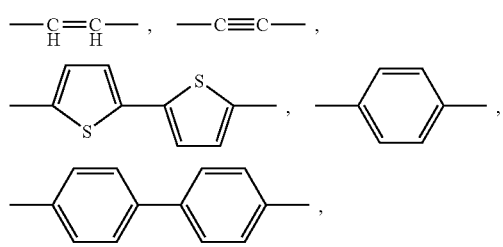

wherein the indolocarbazole moiety is independently selected from the group consisting of structures (A), (B), (C), (D), (E), (F), and (G):

(A)
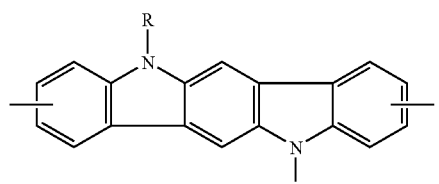

(B)
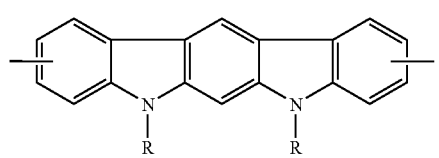

(C)
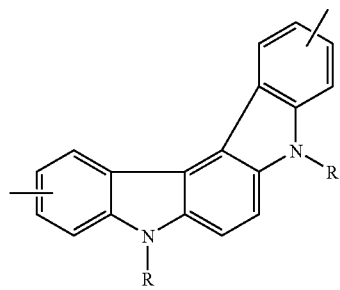

(D)
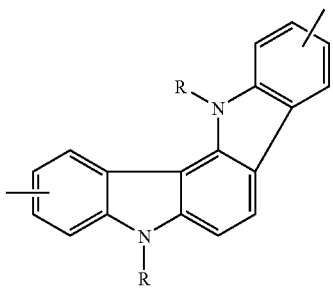

(E)
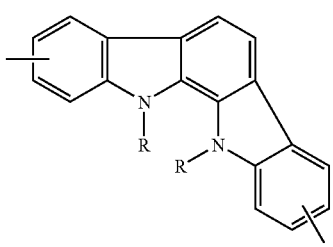

(F)
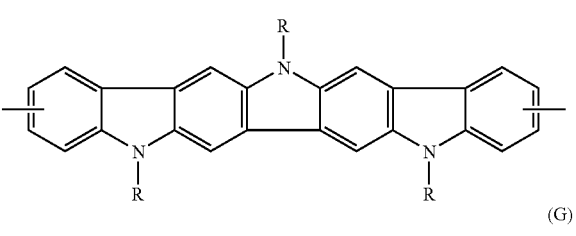

(G)
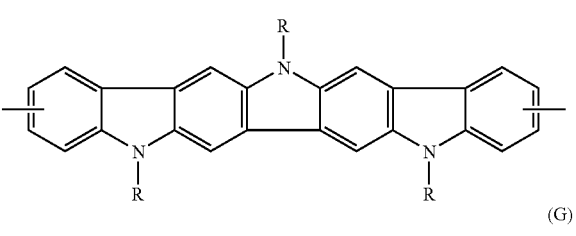

wherein for each of the structures (A) through (G), each R is independently selected from a group consisting of a hydrogen, a hydrocarbon group and a heteroatom-containing group,
   wherein the hydrocarbon group has from 1 to about 30 carbon atoms and is independently selected from the group consisting of: a straight chain alkyl group, a branched alkyl group, a cyclic aliphatic group, an aryl group, an alkylaryl group, and an arylalkyl group,
   wherein the heteroatom-containing group is independently selected from the group consisting of: fluoroalkyl having for example 1 to about 18 carbon atoms, fluoroaryl, cyano, nitro, carbonyl, carboxylate, alkoxy having for example 1 to about 18 carbon atoms, and amino.

2. The small molecule compound of claim 1, wherein the at least one divalent linkage consists of thienylene units.

3. The small molecule compound of claim 1, wherein the at least one divalent linkage is conjugated.

4. The small molecule compound of claim 1, wherein the at least one type of the indolocarbazole moiety is a plurality of indolocarbazole moieties of the same type.

5. The small molecule compound of claim 1, wherein the number of the indolocarbazole moiety regardless of type ranges from 2 to 30; and the number of the at least one divalent linkage regardless of type ranges from 1 to 15.

6. A small molecule compound is selected from the group consisting of:
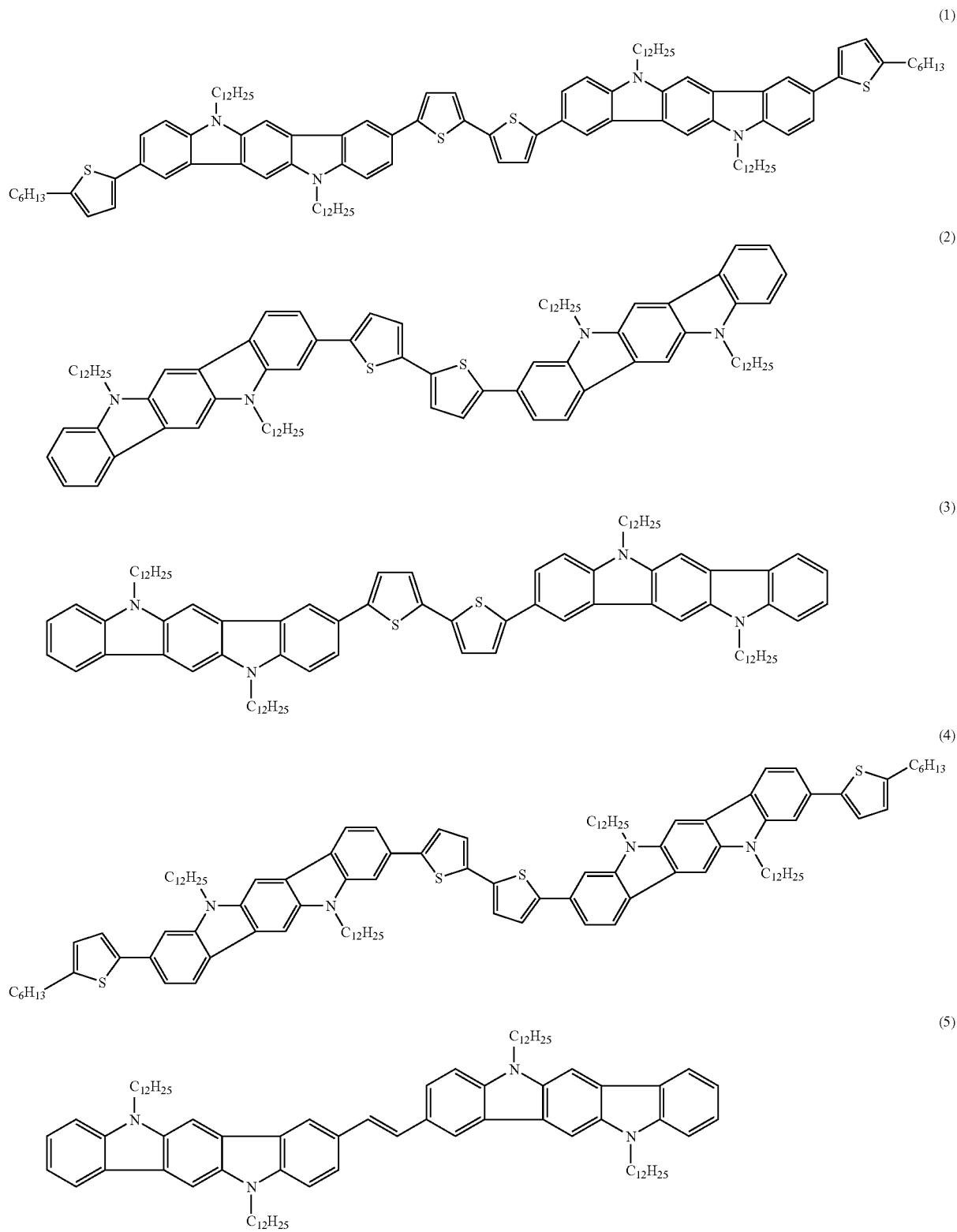

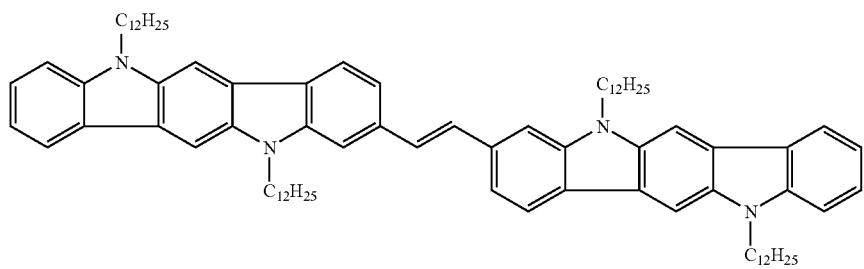
(6)
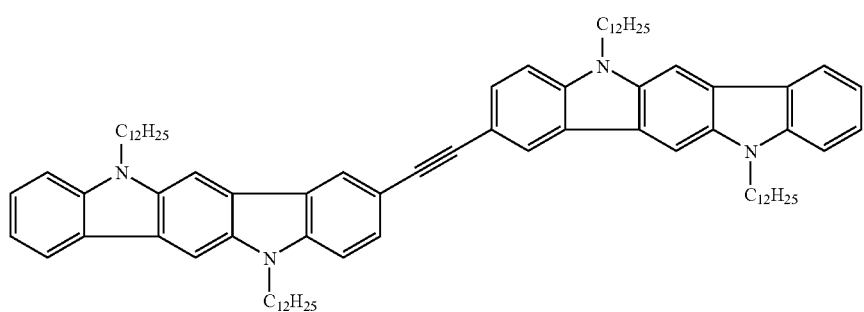
(7)
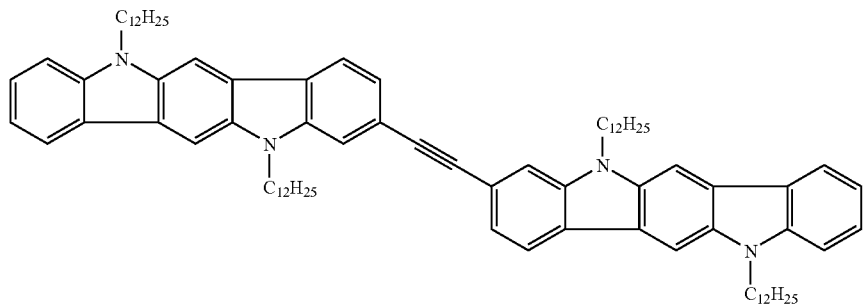
(8)
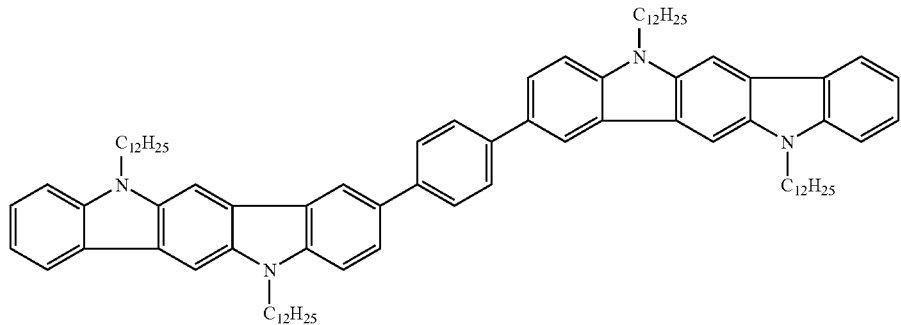
(9)
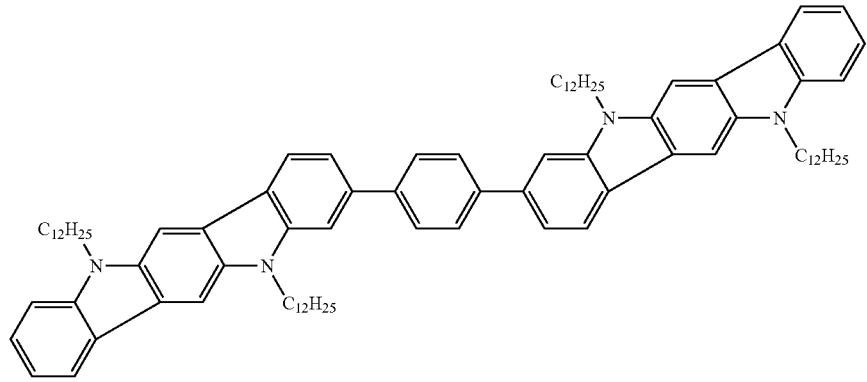
(10)

-continued
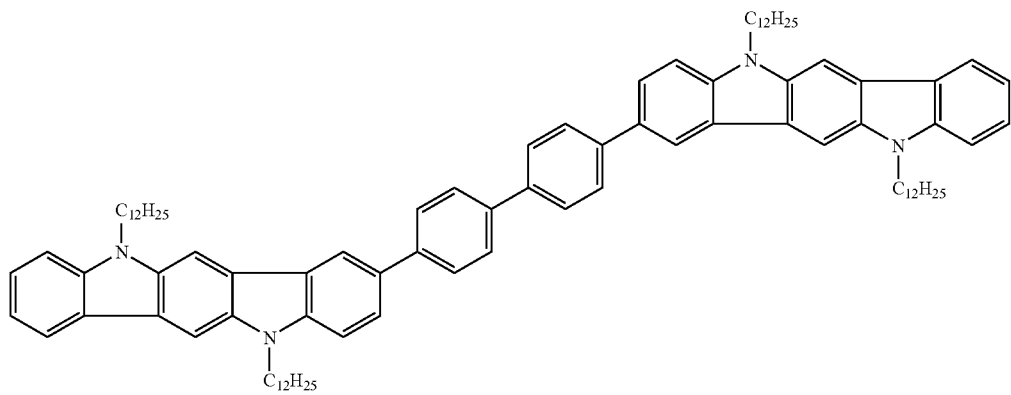
(11)
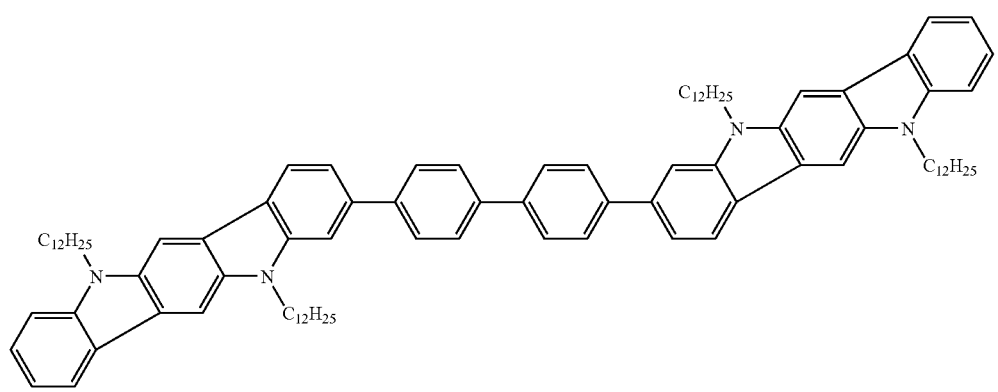
(12)
35
and a mixture thereof.
* * * * *

UNITED STATES PATENT AND TRADEMARK OFFICE
CERTIFICATE OF CORRECTION

PATENT NO. : 7,528,261 B2  
APPLICATION NO. : 11/957927  
DATED : May 5, 2009  
INVENTOR(S) : Yuning Li et al.

Page 1 of 1

It is certified that error appears in the above-identified patent and that said Letters Patent is hereby corrected as shown below:

In the Specification:

Column 1, line 33, after "Cooperative Agreement No.", please delete "70NANBOH3033" and insert --70NANB0H3033--.

Signed and Sealed this  
Tenth Day of September, 2013

Teresa Stanek Rea  
*Acting Director of the United States Patent and Trademark Office*